United States Patent [19]

Damin et al.

[11] 4,413,133
[45] Nov. 1, 1983

[54] PROCESS FOR MANUFACTURING CHLOROLACTONES FROM UNSATURATED CARBOXYLIC ACIDS

[75] Inventors: Bernard Damin, Oullins; Alain Forestiere, Vernaison; Bernard Sillion, Rocquencourt, all of France

[73] Assignee: Institut Francais du Petrole, Rueil-Malmaison, France

[21] Appl. No.: 321,145

[22] Filed: Nov. 13, 1981

[30] Foreign Application Priority Data

Nov. 14, 1980 [FR] France .................... 80 24393

[51] Int. Cl.$^3$ ........................................ C07D 307/32
[52] U.S. Cl. .................... 549/265; 549/273; 549/283; 549/300; 549/302
[58] Field of Search .............. 260/343.6; 549/265, 549/273, 281, 283, 300, 302

[56] References Cited

U.S. PATENT DOCUMENTS 3,870,747  3/1975  Wendler et al. .................... 549/283
4,119,642  10/1978  Larock .................................. 549/265
4,348,535  9/1982  Schmidt ................................ 549/273

OTHER PUBLICATIONS

Chem. Abstracts 75: 77476r.
Chem. Ber. 95,1245, (1962).
Buehler et al., Survey of Org. Synthesis, vol. 2, p. 831, John Wiley & Sons, 1977.
March, Adv. Org. Chem., 2nd Edition, p. 702, McGraw-Hill Book Co., 1977.

*Primary Examiner*—Ethel G. Love
*Attorney, Agent, or Firm*—Millen & White

[57] ABSTRACT

Process for manufacturing chlorolactones by reacting, within an ahydrous organic solvent, a metal N-chlorosulfonamidate of the formula

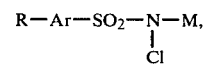

wherein R is a hydrogen or halogen atom or an alkyl radical, Ar is a mono- or polycyclic divalent aromatic radical and M is an alkali metal, with a substantially stoichiometrical proportion of an aliphatic or alicyclic carboxylic acid having at least one double bond separated from the COOH group by at least 2 carbon atoms, in the presence of a substantially stoichiometrical amount of a strong acid whose conjugate base is weakly nucleophilic.

9 Claims, No Drawings

PROCESS FOR MANUFACTURING CHLOROLACTONES FROM UNSATURATED CARBOXYLIC ACIDS

BACKGROUND OF THE INVENTION

This invention concerns the synthesis of chlorolactones from unsaturated carboxylic acids.

The resultant chlorolactones may be used generally as intermediary synthesis products in organic chemistry or, more particularly in so far as regards γ-chloromethyl γ-butyrolactone or δ-chloromethyl δ-valerolactone, as solvents, for example for acetylene, for epoxy resins, for polyvinyl chloride and its copolymers or still for other resins.

The halolactonization reaction is known since the beginning of the century and is still of interest in synthetic organic chemistry. See for example M. D. DOWLE and D. I. DAVIES, Chem. Soc. Rev., 8 (2), 171 (1979).

Whereas the bromo-and iodolactones obtained by reacting halogen, in basic medium, on an unsaturated acid according to the scheme below, have been largely described, no example is known of a direct and selective conversion of unsaturated acids to chlorolactones in an economical way; the lactonization reaction is, as a matter of fact, in competition with the dichlorination reaction as indicated in the following references: E. E. VAN TAMELEN & M. SHAMMA, J. Am. Chem. Soc., 76, 2315 (1954); G. BERTI, Gazzeta, 81, 305 (1951); G. BERTI, Tetrahedron, 4, 393 (1958); W. REPPE, O. SCHLICHLING, K. KLAGER & T. TOEPEL, Annalen, 560, 1 (1948); R. ODA, S. MUNEIMIYA & M. OKANO, J. Org. Chem., 26 (5), 1341 (1961); G. F. BLOOMFIELD & E. H. FARMER, J. Chem. Soc., 2062 (1932); and U.S. Pat. No. 4,031,115.

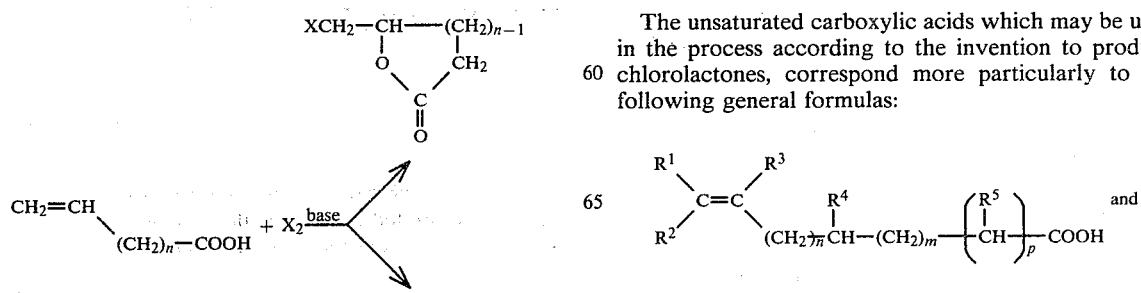

In these formulae, X is a halogen atom and n is an integer, for example from 1 to 12.

B. DAMIN, J. GARAPON and B. SILLION, Tetr. Letters 21, 1709 (1980), have recently described a chloroxy-carboxylation of olefins by reaction of "T chloramine" (sodium N-chloro-para- toluenesulfonamidate) in the presence of a carboxylic acid, according to the following scheme:

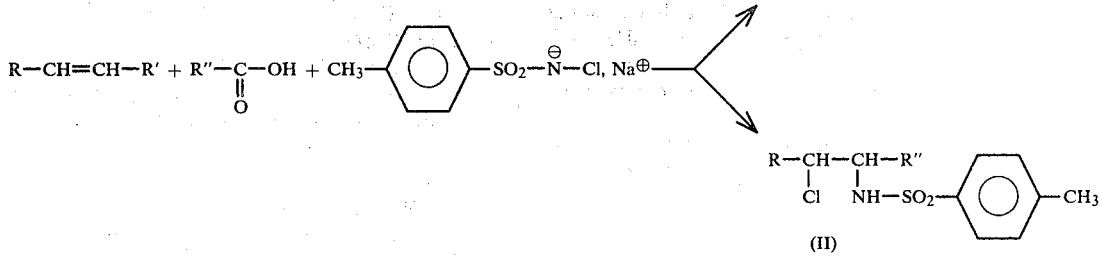

wherein each of R and R' represents a hydrogen atom or an aromatic or aliphatic hydrocarbon radical having from 1 to 8 carbon atoms and R" is an aliphatic radical having from 1 to 5 carbon atoms.

However, as is apparent from the reaction scheme, the chloroxycarboxylation reaction is accompanied by the formation of a chlorotosylation product (II) with yields which may reach 15%.

It has now been discovered that it is possible to form chlorolactones with high yields and without secondary chlorotosylation or dichlorination reactions.

SUMMARY OF THE INVENTION

As a general rule, the process for manufacturing chlorolactones according to the invention comprises reacting, advantageously in an anhydrous organic solvent, a metal N-chlorosulfonamidate with an unsaturated carboxylic acid whose unsaturation is separated from the carboxylic group by at least two carbon atoms, in the presence of a strong acid (whose conjugate base is a weak nucleophilic compound), said strong acid being used to displace from the metal N-chlorosulfonamidate the corresponding acid which constitutes the reactive species.

DETAILED DISCUSSION

The unsaturated carboxylic acids which may be used in the process according to the invention to produce chlorolactones, correspond more particularly to the following general formulas:

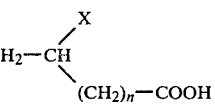

-continued

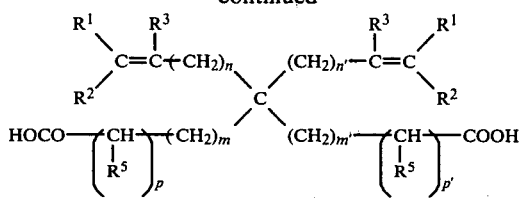

wherein each of $R^1$, $R^2$, $R^3$, $R^4$ and $R^5$ represents a hydrogen atom or an alkyl, linear or branched, radical having from 1 to 30 carbon atoms; they may be also associated together to form hydrocarbon bridges; n, m and p are integers from 0 to 12 whose sum is from 1 to 12, n', m' and p' are integers from 0 to 12 whose sum is from 1 to 12.

Preferably, n and m, each have a value of 0, 1 or 2 and p a value of 0 or 1, the sum n+m+p being from 1 to 5. The same is true for n', m' and p'.

Examples of unsaturated carboxylic acids which can be used in the process of the invention are: allylacetic acid (or 4-pentenoic acid), 5-hexenoic acid, 3-cyclohexene carboxylic acid, (2.2.2) bicyclo 5-octene 2-carboxylic acid and di-allyl malonic acid.

The N-chlorosulfonamidates used in the process according to the invention are more particularly those complying with the general formula:

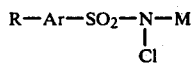

wherein R is a hydrogen atom, an alkyl radical, preferably linear, containing for example from 1 to 10 carbon atoms, or a halogen atom, preferably chlorine; Ar is a divalent aromatic radical containing one or more cycles, preferably a phenylene radical, whose substituents are in ortho, meta or para position; and M is an alkali metal, preferably sodium.

As metal N-chlorosulfonamidates, there are advantageously used, according to the invention, products of industrial grade such as sodium N-chlorobenzenesulfonamidate (or "B chloramine"), sodium N-chloroparatoluenesulfonamidate (or "T chloramine") and sodium N-chloroparachlorobenzenesulfonamidate (or "C chloramine").

Strong acids which can be used, as a general rule, in the process of the invention are those whose dissociation in the solvent involved, results in a pKa smaller by about 2 units than the pKa, determined in the same solvent, of the N-chlorosulfonamide acid corresponding to the metal N-chlorosulfonamidate involved. In practice, any acid whose pKa in water is smaller than 2.5 can be used (the pKa of N-chloroparatoluene sulfonamide acid in water at 20° C. is about 4.5). Main examples of such acids are sulfuric acid, phosphoric acid, and sulfonic acids such as arylsulfonic or alkylsulfonic acids.

In the process of the invention, the metal N-chlorosulfonamidate is generally used in a proportion of about 1 mole per mole of unsaturated carboxylic acid, and the strong acid is generally used in a proportion of 1 mole per mole of metal N-chlorosulfonamidate.

When carrying out the process according to the invention, it is important to use the N-chlorosulfonamidates in anhydrous medium and the operation will be advantageously conducted in an aromatic, aliphatic or alkylaromatic organic solvent or in a conventional halogenated solvent. Advantageously benzene or chlorobenzene are used.

In practice, the metal N-chlorosulfonamidate is suspended in the selected anhydrous organic solvent. Then, the carboxylic acid and the strong acid are simultaneously added while adjusting the flow rates of the two reactants in such a manner that the temperature of the reaction medium does not exceed 50° C. The mixture is then brought to a temperature from 50° to 130° C. for a period from 0.5 to 10 hours, according to the case. After cooling, washing and filtration, the obtained chlorolactone is separated by distillation or by chromatography through a column, for example a column of silica. The chlorolactones are obtained with high yields of pure products.

The nature of the obtained products may be determined by different methods of analysis: infra-red spectrography, proton nuclear magnetic resonance, carbon 13 nuclear magnetic resonance, mass spectrography and elementary analysis; these methods confirm the "chlorolactone" structure.

The chlorolactones obtained by the above-described process are, in most cases, new products. Thus, for example, δ-chloromethyl-δ-valerolactone, 4-chlorocyclohexane 1-carbolactone (3) and 3-chloro cyclohexane 1-carbolactone (4),3-chloro-(2.2.2)bicyclooctane 6-carbolactone (2) and α-spiro bis(γ-chloromethyl-γ-butyrolactone) in the form of an equimolecular mixture of the two stereoisomers.

As in the case of γ-chloromethyl γ-butyrolactone, these chlorolactones may be used as solvents for various organic materials, particularly polymers.

On the other hand, the chlorolactonization reaction and the chlorolactones may be involved in various organic synthesis processes.

For example, advantage may be taken of the chlorolactonization reaction of unsaturated carboxylic acids, conducted as abovedescribed, to separate two isomers whose chlorolactonization velocities are different. If so desired, it will be possible to recover the carboxylic acids, which are then generally the saturated acids, by a reaction of the following type:

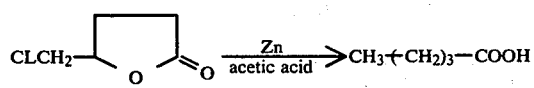

It is also possible, from the chlorolactones, to obtain the corresponding dehalogenated lactones according to the following reaction scheme:

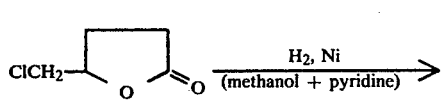

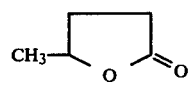

It is also possible to make use of the chlorolactones to obtain unsaturated lactones which are potential antitumor agents, according to the following reaction scheme:

wherein DBU is diazo-bicyclo-undecane and DBN is diazobicyclononene.

The following examples illustrate the invention, but must not be considered in any way as limiting the scope thereof.

The structure of the products obtained in each of these examples has been confirmed by elementary analysis, infrared spectrography, proton nuclear magnetic resonance, carbon 13 nuclear magnetic resonance, and mass spectrography.

EXAMPLE 1

To a suspension of 23.9 g (0.105 mole) of anhydrous "T Chloramine" in 80 ml of anhydrous benzene, there is simultaneously added, dropwise, 10.1 g (0.1 mole) of allylacetic acid and 10.1 g (0.105 mole) of methanesulfonic acid.

The reaction is very exothermic and the addition step is so controlled that the temperature does not exceed 50° C. At the end of the addition step, the reaction mixture is brought to 80° C. for 5 hours. After return to room temperature and filtration of the insoluble part, which is washed with some benzene, the solvent is evaporated. The γ-chloromethyl γ-butyrolactone is separated by direct distillation or by passage over a silica column and elution with methyl chloride followed by distillation. B.P. $10^{-2}$ Torr=65°–66° C. The yield of purified product is 63%.

EXAMPLE 2

The operating conditions are identical to those of example 1. There is used 23.9 g (0.105 mole) of anhydrous "T Chloramine", 80 ml of anhydrous chlorobenzene, 14.85 g (0.1 mole) of 5-hexenoic acid and 10.1 g (0.105 mole) of methanesulfonic acid. After 2 hours at 110° C. and a treatment similar to that of example 1, δ-chloromethyl δ-valerolactone is distilled.

B.P. $10^{-2}$ Torr=72°–73° C. The yield of purified product is 61%.

EXAMPLE 3

Identical operating conditions are used with 22.8 g (0.1 mole) of anhydrous "T Chloramine", 80 ml of anhydrous chlorobenzene, 12.6 g (0.1 mole) of 3-cyclohexene 1-carboxylic acid and 9.6 g (0.1 mole) of methanesulfonic acid. After one hour at 80° C. and with a treatment identical to that described in example 1, chlorolactone is separated by distillation; two isomers are isolated: 4-chloro cyclohexane 1-carbolactone (3) and 3-chloro cyclohexane 1-carbolactone (4). The products are purified by recrystallization (melting point: 125° C. and 86° C.). The total yield of purified chlorolactones is 58%.

EXAMPLE 4

The operating conditions are identical to those of the preceding examples with the use of 4.55 g ($2.10^{-2}$ mole) of anhydrous "T Chloramine", 20 ml of anhydrous chlorobenzene, 3.04 g ($2.10^{-2}$ mole) of (2,2,2)-bicyclo 5-octene 2-carboxylic acid and 19.2 g ($2.10^{-2}$ mole) of methanesulfonic acid, at 80° C. for 3 hours. After filtration of the reaction mixture and evaporation of the solvent, the (2,2,2) bicyclo 3-chloro octane 6-carbolactone (2) is separated by distillation.

B.P. $10^{-2}$ Torr=115° C. The yield of purified product is 77%.

EXAMPLE 5

In an identical manner, 11.4 g ($5.10^{-2}$ mole) of anhydrous "T Chloramine", 60 ml of anhydrous chlorobenzene, 4.6 g (2.5 $10^{-2}$ mole) of diallyl malonic acid and 4.8 g ($5.10^{-2}$ mole) of methanesulfonic acid are reacted at 80° C. for 3 hours; after filtration and evaporation of the solvent, the α-spiro-bis-(γ-chloromethyl γ-butyrolactone) is separated in a silica column by elution with methyl chloride. The product is then recrystallized (melting point 95° C.). The yield of purified product is 74%. The product consists of an equimolecular mixture of the two stereoisomers.

What is claimed is:

1. A selective, one-step process for manufacturing chlorolactones by chlorolactonization of unsaturated carboxylic acids, comprising reacting, in an anhydrous organic solvent, a metal N-chlorosulfonamidate of the general formula:

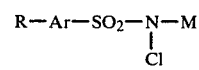

wherein R is a hydrogen atom, an alkyl radical or a halogen atom; Ar is a divalent aromatic radical containing one or more rings; and M is an alkali metal, with an aliphatic or alicyclic carboxylic acid having at least one ethylenic unsaturation separated from the carboxyl group by at least two carbon atoms, in the presence of a strong acid whose conjugate base is weakly nucleophilic.

2. A process according to claim 1, wherein the metal N-chlorosulfonamidate is suspended in an anhydrous organic solvent and the unsaturated carboxylic acid and the strong acid are each added in a substantially stoichiometrical proportion with respect to the metal N-chlorosulfonamidate, at a temperature lower than about 50° C.; the resultant reaction mixture is then heated at a temperature from 50° to 130° C. for 0.5 to 10 hours; and the resultant chlorolactone is separated from the reaction medium and purified.

3. A process according to claim 1, wherein said carboxylic acid with ethylenic unsaturation has the formula

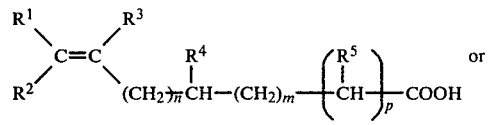

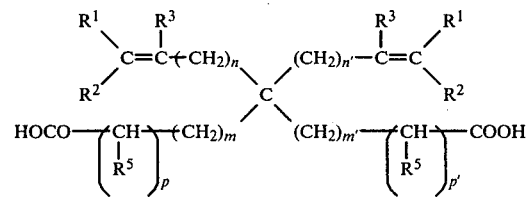

wherein $R^1$, $R^2$, $R^3$, $R^4$ and $R^5$ are each independently H, $C_{1-30}$ alkyl or may be interconnected to form carbon bridges; n, m and p are each integers from 0 to 12, the sum of which is from 1 to 12; and n', m' and p' are each integers from 0 to 12, the sum of which is from 1 to 12.

4. A process according to claim 3, wherein, in the formulae of the carboxylic acids with ethylenic unsaturation, n and m each has a value selected from 0 to 2, p has a value of 0 or 1, the sum n+m+p being from 1 to 5, n' and m' each has a value from 0 to 2 and p' has a value of 0 or 1, n'+m'+p' being from 1 to 5.

5. A process according to claim 3, wherein said carboxylic acid with ethylenic unsaturation is selected from allylacetic acid, 5-hexenoic acid, 3-cyclohexene 1-carboxylic acid, (2.2.2)bicyclo 5-octene 2-carboxylic acid and diallylmalonic acid.

6. A process according to claim 1, wherein said metal N-chlorosulfonamidate is selected from sodium N-chlorobenzenesulfonamidate, sodium N-chloroparatoluenesulfonamidate and sodium N-chloroparachlorobenzenesulfonamidate.

7. A process according to claim 1, wherein said strong acid has a pKa in the solvent involved 2 units lower than the pKa, in the same solvent, of the acid corresponding to said metal N-chlorosulfonamidate.

8. A process according to claim 1, wherein said strong acid is sulfuric acid, phosphoric acid or an aryl- or alkylsulfonic acid.

9. A process according to claim 1, wherein the solvent is benzene or chlorobenzene.

* * * * *